(12) United States Patent
Stumpel

(10) Patent No.: US 7,905,726 B2
(45) Date of Patent: Mar. 15, 2011

(54) SURGICAL GUIDE FOR DENTAL IMPLANT AND METHODS THEREFOR

(76) Inventor: Lambert J. Stumpel, San Francisco, CA (US)

( * ) Notice: Subject to any disclaimer, the term of this patent is extended or adjusted under 35 U.S.C. 154(b) by 48 days.

(21) Appl. No.: 11/870,310

(22) Filed: Oct. 10, 2007

(65) Prior Publication Data

US 2008/0176187 A1    Jul. 24, 2008

Related U.S. Application Data

(60) Provisional application No. 60/850,605, filed on Oct. 10, 2006.

(51) Int. Cl.
    A61C 13/34    (2006.01)
    A61C 19/04    (2006.01)
(52) U.S. Cl. ............................ 433/75; 433/196; 433/215
(58) Field of Classification Search .......... 433/72–76, 433/173, 174, 196, 215; 606/96, 97
    See application file for complete search history.

(56) References Cited

U.S. PATENT DOCUMENTS

| | | | | |
|---|---|---|---|---|
| 1,407,840 | A | * | 2/1922 | Cruttenden ...................... 433/76 |
| 5,015,183 | A | | 5/1991 | Fenick |
| 5,320,529 | A | | 6/1994 | Pompa |
| 5,556,278 | A | | 9/1996 | Meitner |
| 5,575,656 | A | * | 11/1996 | Hajjar ............................ 433/219 |
| 5,800,168 | A | * | 9/1998 | Cascione et al. ................ 433/75 |
| 5,833,693 | A | * | 11/1998 | Abrahami ........................ 606/96 |
| 6,537,067 | B1 | * | 3/2003 | Wennemann ..................... 433/76 |
| 6,634,883 | B2 | | 10/2003 | Ranalli |
| 6,644,969 | B2 | | 11/2003 | Kumar |
| 6,824,384 | B1 | | 11/2004 | Bompard et al. |
| 6,869,283 | B2 | | 3/2005 | Sussman |
| 6,913,463 | B2 | | 7/2005 | Blacklock |

(Continued)

FOREIGN PATENT DOCUMENTS

CA    2 484 475    4/2006

OTHER PUBLICATIONS

"CADImplant—Implanting with Ease™", 2004, CADImplant, Inc., Champfeuillet, France.

(Continued)

*Primary Examiner* — Cris L Rodriguez
*Assistant Examiner* — Michael R Ballinger
(74) *Attorney, Agent, or Firm* — Morgan, Lewis & Bockius LLP; Victor E. Johnson

(57) ABSTRACT

A surgical guide assembly is provided for positioning a drill bit during a dental implant procedure. The guide assembly includes a mounting member configured to mount to one or more teeth adjacent to an edentulous area, a base connected to the mounting member and dimensioned to extend over the edentulous area, a translation member adjustable with respect to the base, and a rotation member adjustable with respect to the translation member. The rotation member includes an aperture configured to receive a radiographic marker or a drill. The translation and rotation members may be configured to adjust one of the mesio-distal (MD) rotational alignment and the buccal-lingual (BL) rotational alignment of the radiographic marker inserted in the aperture while holding the other of the MD and BL rotational alignment mechanically fixed. Also, the translation and rotation members may be configured to adjust the other of the MD and BL translational alignment of the radiographic marker while holding said one of the MD and BL translational alignment mechanically fixed. A method of using the dental implant positioning assembly is also disclosed.

10 Claims, 11 Drawing Sheets

U.S. PATENT DOCUMENTS

| | | | |
|---|---|---|---|
| 6,971,877 B2 * | 12/2005 | Harter | 433/75 |
| 7,014,461 B2 * | 3/2006 | Weinstein | 433/76 |
| 7,044,735 B2 | 5/2006 | Malin | |
| 7,086,860 B2 | 8/2006 | Schuman et al. | |
| 7,097,451 B2 | 8/2006 | Tang | |
| 2004/0219479 A1 * | 11/2004 | Malin et al. | 433/75 |
| 2005/0142517 A1 | 6/2005 | Frysh et al. | |
| 2006/0257817 A1 | 11/2006 | Shelton | |
| 2006/0281046 A1 | 12/2006 | Heo | |
| 2007/0059661 A1 | 3/2007 | Dadi | |
| 2007/0154862 A1 * | 7/2007 | Kim | 433/72 |

OTHER PUBLICATIONS

"iDent—ImplantMaster", 2007, http://www.ident-surgical.com/tec_01.htm.

"Iit—Innovative Implant Technology", 2006, http://www.iitweb.com/product/description/IGS.

"Materialise Dental—Tooth Supported SurgiGuide", 2006, Materialise Group, Leuven, Belgium.

"NobelGuide™ Options", 2008, http://www.nobelbiocare.com/global/en/ClinicalProcedures/NobelGuide/options.htm.

* cited by examiner

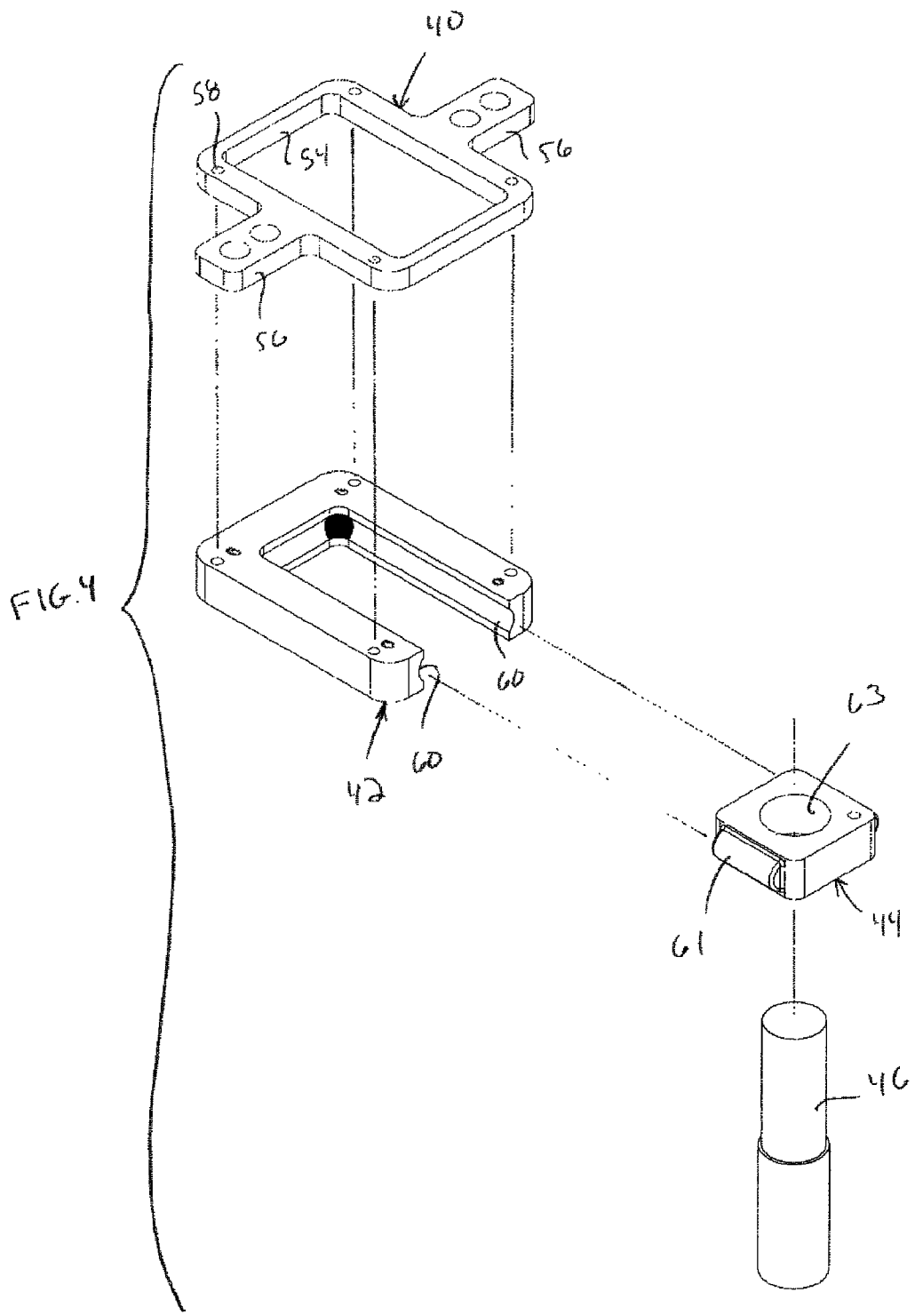

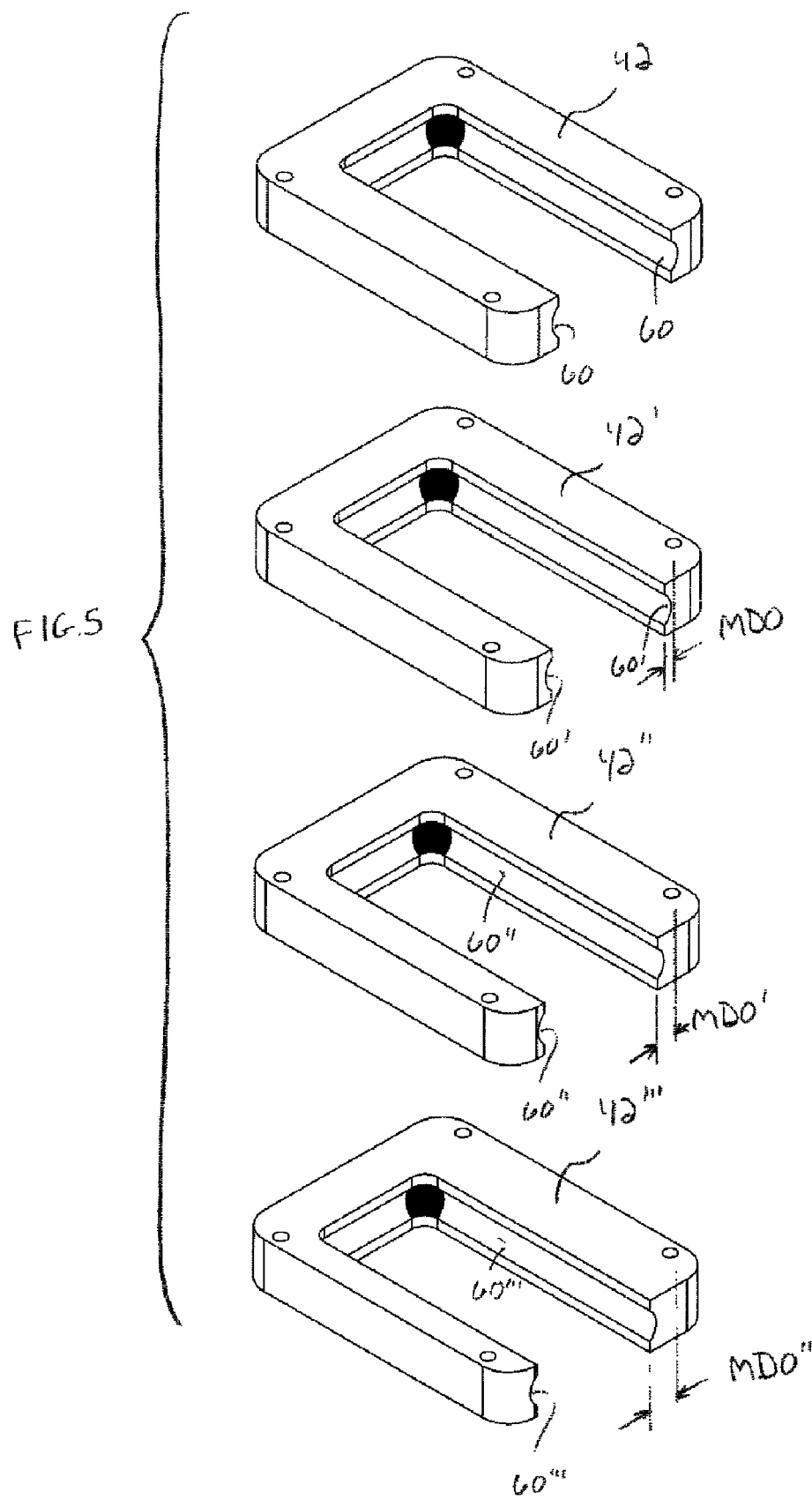

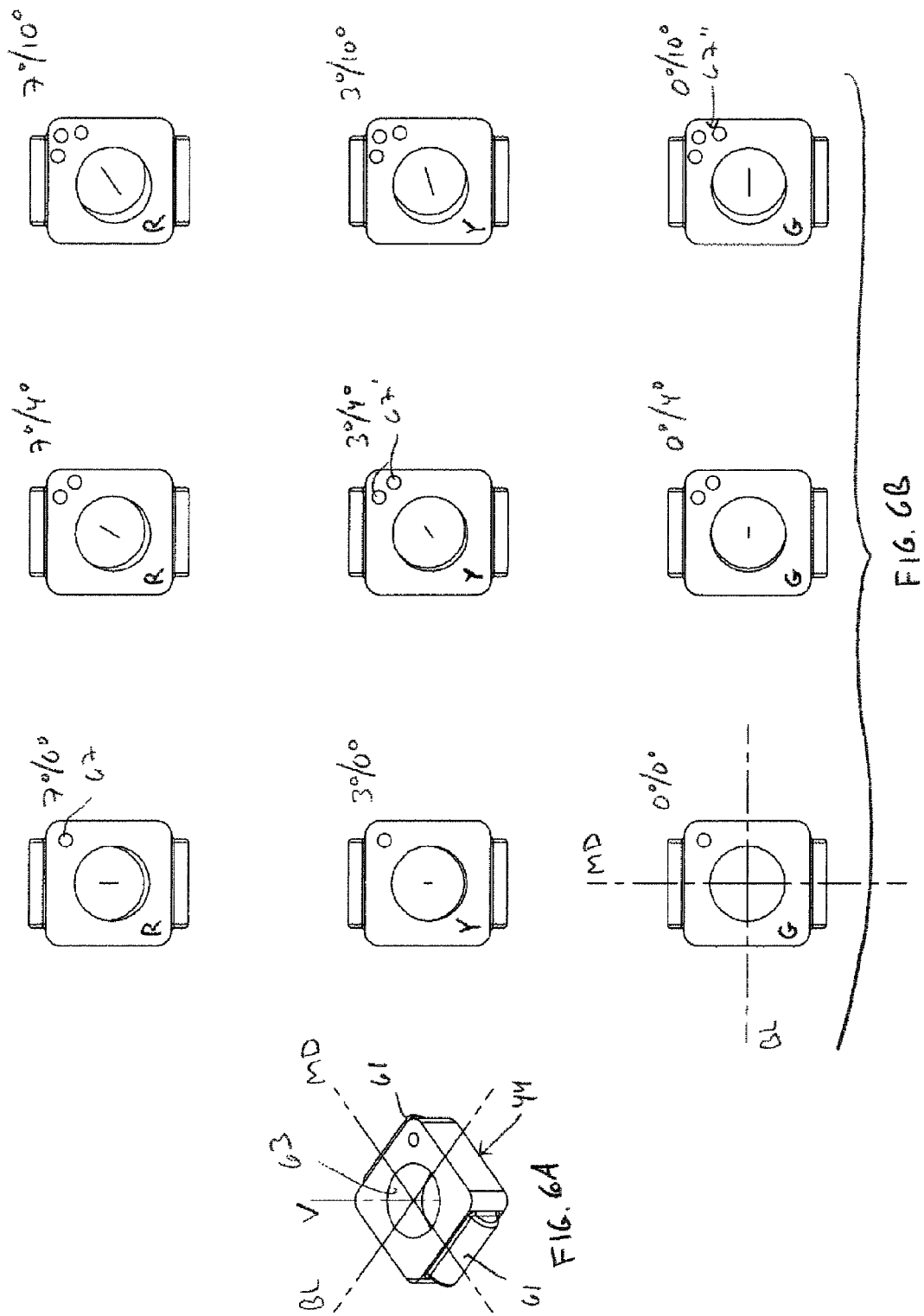

SURGICAL GUIDE FOR DENTAL IMPLANT AND METHODS THEREFOR

CROSS-REFERENCES TO RELATED APPLICATIONS

This application claims priority to U.S. Provisional Patent Application No. 60/850,605 filed Oct. 10, 2006, entitled Implant Positioning System Model Based, the entire contents of which application is incorporated herein by this reference.

BACKGROUND OF THE INVENTION

1. Field of the Invention

The present invention relates to a method of positioning a dental implant at an implant site. More particularly, the present invention relates to method of positioning a dental implant utilizing a dental cast, preparing a surgical guide, using the surgical guide as is, or in conjunction with the drilling of a model osteotomy, allowing pre-fabrication of an abutment and/or a temporary crown, and intra-oral placement of the dental implant.

2. Description of Related Art

Dental implants are an increasingly popular option for patients with missing teeth due to excessive decay, bone or gum damage, or accidents causing physical displacement and the like. Dental implants provide an attractive alternative to dentures because they look natural and require less maintenance. Implants further provide a stronger biting surface and allow patients to resume their normal diets.

In comparison to dentures and the like, however, dental implant procedures involve costly and complex surgical work. More accurately, dental implant procedures generally involve the placement of a dental implant or abutment in the underlying jawbone as a foundation, and the subsequent attachment of a prosthetic to the implant above the gum line. Generally, a dental osteotomy must be performed to prepare the bone for placement of the implant in order to place the implant. The implant is then inserted and fixed into the bone where it serves to hold the dental prosthetic. Accordingly, the osteotomy and implant placement must be precise.

The most difficult and skill intensive part of the implant procedure is generally positioning the drill to create the hole in the jawbone that will receive the implant. The hole must be formed at the precise location relative to adjacent teeth for a natural, attractive look. The hole must also be positioned in the proper location in the bone to ensure a solid base for the prosthetic. Inaccuracies in placing the hole can damage nearby vital structures such as nerves, blood vessels, sinus and neighboring teeth.

Improper placement of the hole for the implant also presents problems for the surgeon during the implant procedure. If the hole is not placed in the proper position in the jawbone, further drilling may be necessary. Even more troublesome, if bone has been mistakenly removed, new bone may have to be grafted or added to the site and let to heal for 3-6 months before a new attempt can be made.

For these reasons, implant procedures typically require the expertise of oral surgeons and usually are avoided by general dentists. Even some oral surgeons hesitate to do implant procedures because of the unique skills and experience required.

Positioning mistakes also require additional office visits by the patient, additional time to completion, and unnecessary discomfort. For this reason, it is highly desirable to reduce the risk of mistakenly drilling in an incorrect position.

Many tools and methods exist for increasing the accuracy, reliability, and ease with which a surgeon can perform the drilling operation. The most popular technique remains free-hand alignment. In the case of free-hand drilling, a surgeon draws upon his or her experience to determine the proper trajectory and final location of the implant. Not only does this require a steady hand, but the surgeon must also make a judgment as to where the bone is located below gum surface. Because the bone is masked under the gum tissue and because it is difficult to fully inspect the site, the surgeon typically has great difficulty in determining the proper position in this initial step.

The flap method is the typical method for overcoming the problem of determining bone position below the gum line. The flap method involves physically cutting a flap of skin near the site and surveying the implant site to determine the position of the jawbone. This method increases the risk of infection and provides further discomfort for the patient.

Free-hand drilling also presents safety hazards and accuracy problems. Although the surgeon can initially determine where to drill, during the drilling procedure, the drill bit can "jump" or slip. The drill bit can also "walk" or move before the tip of the bit grabs or digs into the bone. Additionally, free-hand drilling requires the surgeon to act without a complete view of the mouth interior and implant site.

Model-based or lab-based methods allow improved positioning by allowing less invasive surveying of the implant site. This method also provides for transferring of the measurements from the cast to the actual site. An exemplar of the prior art is U.S. Pat. No. 7,086,860 to Schuman et al. The Schuman method involves using tools to determine the size, angles, and positions for the dental implant on a model cast. The cast is cut to determine the bone position. A graphic is then drawn on the model and tools are used to transfer the placement information of the graphic to the implant site. In the laboratory, the buccal-lingual ("BL") volume of bone is derived from the subtraction of the tissue depth as measured in the mouth through bone sounding. If the anatomy is followed, an accurate reflection of the available bone volume for implant placement may be determined. The mesio-distal ("MD") positioning of the implant is derived from the transpositioning or translation of information from a radiograph onto the cast.

The above method has several limitations. The MD positioning in the lab is only an estimate and is not verifiable until transferred to a model and the mouth. Also, this method only allows the surgeon to practice drilling on a model and does not assist with transferring or accurately mapping the determined drilling position from the model back to the implant site. Cast models also do not overcome the drilling problems mentioned above.

U.S. Pat. No. 5,556,278 to Meitner is directed to a template to allow a surgeon to more accurately transfer the drilling location determined on the model to the implant site in the mouth. Meitner describes a tooth setup molded around the implant site and then placed on a cast model. The surgeon then drills through the setup. A guide post is inserted through the hole, and a sleeve is inserted over the guide post. A resin is then placed over the entire site with a separating medium between the resin and model. Once the resin dries, the resin is removed and can be used as a template to transfer the exact location from the model to the implant site. Further, the guide sleeve may act as a radiographic marker so the surgeon can determine the location and trajectory of the hole to be made in the bone by taking an X-ray with the template in place in the mouth.

Although the Meitner apparatus allows for relatively precise transfer of a drill location from a model to the implant site, errors still arise due to variations between the model and implant site. Further, the surgeon may decide on a position using the model and later reconsider when the template and sleeve are filmed at the implant site. In this case, the template must be formed again from the start and the patient will be required to make extra visits to the office and wait longer.

Another technique is based upon determining a trajectory for the drill using tools and aids and then translating the trajectory information to the implant site. An exemplar of such a technique is U.S. Pat. No. 5,015,183 to Fenick. Using X-rays, the surgeon determines where the implant should be positioned in the bone and then uses bushings to help guide the drill bit. Fenick also creates a radiology stent that includes a opaque grid. The stent, without any drill bushings, is X-rayed while in the patient's mouth. The stent is then placed over a model of the patient's jaw where the grid provides a frame of reference that helps in manually positioning a drill bit relative to the model jaw. A hole is drilled into the model, and the resulting hole helps align a drill bushing relative to the model. Next, a cast is created over the model to capture the drill bushing. The cast, with the drill bushing, is then placed in the patient's mouth to help guide the drill bit that drills a hole into the patient's jawbone. With the Fenick system, some positional accuracy may be sacrificed because the drill bushing is aligned to a model rather than being aligned directly to the patient's actual jaw.

In more recent years, computers and sophisticated peripheral imaging equipment have caused the positioning of implant systems to become far more sophisticated. Using radiographic and visual images of the mouth, one can construct detailed computer models such as computer aided drafting (CAD/CAM) drawings. The computer allows technicians and surgeons to experiment with many different positions and trajectories in three-dimensional computer space. A computer also allows a user to input various variables into the procedure and calculate the exact trajectory for the drill. Moreover, once the model is constructed and trajectory calculated, the data can be used to prototype a surgical guide for the drill.

Thus, computers in combination with many of the above procedures allow surgeons and technicians great flexibility in preparing for the osteotomy and implant procedure. These tools also allow the accurate translation of the data from the model to the implant site. However, such equipment can be extremely costly. Also, sophisticated equipment requires sophisticated technical skills and may be beyond the reach of those with limited technology skills.

Another method for performing implant osteotomies provides a method for readjusting the drill trajectory directly in the mouth. U.S. Pat. No. 7,097,451 to Tang describes a thermoplastic surgical template that allows adjustment after initially setting a drill position. The Tang template includes a base and a drill guide. The alignment of the drill guide may be determined using conventional methods. Alternatively, the template may be fastened in the mouth without setting an initial drill position.

The Tang template is constructed of a thermoplastic chosen with thermo-properties such that it can be heated to a state whereupon it can be molded. The thermoplastic then hardens when it cools. Thus, the surgeon can place the template, heat the template, readjust the drill guide with a specified tool, and then allow it to harden at the determined position. This process minimizes the number of office visits and steps in the osteotomy procedure. Surgeons can easily adjust the template at will without going through lots of steps or fabricating procedures.

Although the Tang template allows a surgeon to combine modeling with relatively accurate translation of the data to the implant site, such templates and methods lack readjustment control. The surgeon can readjust the template at the mouth site, but readjustment amounts to free-hand alignment. Once the thermoplastic is heated to a moldable state, the template flows freely in all directions. Essentially, the surgeon must reposition the drill guide in free space, meaning, in three dimensions with 360° of rotation. Additionally, the abutment and temporary crown can only be made after the surgical guide has been approved clinically because of the liberal readjustment procedure. Similar to the other methods described, the Tang method does not provide a controllable and quantifiable method of positioning relative to a dental cast.

In light of the forgoing, it would be beneficial to have a method and apparatus for aligning a dental implant which overcomes the above and other disadvantages of known implant positioning systems and methods. What is needed is an improved method and apparatus for controllably and quantifiably determining and adjusting a desired drilling trajectory that would allow accurately and repeatably performing a dental implant osteotomy and placing of a laboratory analog of an implant.

BRIEF SUMMARY OF THE INVENTION

In summary, one aspect of the present invention is directed to a method of preparing a surgical guide for positioning a dental implant relative to an implant site, said method including one or more of the following steps: providing an alignment assembly, said alignment assembly including a mounting member configured to mount to one or more teeth adjacent to an edentulous area of the implant site, a base connected to the mounting member and dimensioned to extend over the edentulous area, a translation member adjustable with respect to the base, and a rotation member adjustable with respect to the translation member, said rotation member including an aperture configured to receive a radiographic marker or a drill; inserting the radiographic marker through the rotational member; placing the alignment assembly at the edentulous area where the dental implant is to be placed; adjusting the mesio-distal (MD) rotational alignment of the radiographic marker while holding the buccal-lingual (BL) rotational alignment mechanically fixed; and adjusting the MD translational alignment of the radiographic marker while holding the BL rotational alignment mechanically fixed.

The method may further include the steps of: placing the alignment assembly on a model of the edentulous area; adjusting the BL rotational alignment of the radiographic marker while holding the MD rotational alignment mechanically fixed; and adjusting BL translational alignment of the radiographic marker while holding the MD translational alignment mechanically fixed. The method may further include the steps of: inserting a guide member in place of the radiographic marker; modeling drilling of a jaw bone on a model of the implant site using the alignment assembly; and evaluating the position of the guide member relative to the implant site. The method may further include the steps of: fabricating a surgical guide based on the alignment assembly whereby the guide member in the alignment assembly may be used to guide a drill in a mouth; and placing the surgical guide at the implant site.

The mounting member may be formed of an impression material spatially setting the base relative to the edentulous area. The base and the translation member may be configured such that the translation member can adjustably translate in a longitudinal direction relative to the base member for adjustment of MD translational alignment.

The translation member may be selected from a set of translation members having incremental MD offsets, wherein MD translational alignment may be adjusted by selecting a respective one of said set having a desired MD offset. The set of translation members may be reversible such that turning a respective one of said set upside-down provides a negative MD offset. The translation member and the rotation member may be configured such that the rotation member can adjustably translate in a lateral direction relative to the translation member for adjustment of BL translational alignment.

The rotation member may be rotationally fixed when laterally adjusted within the translation member. The rotation member may be selected from a set of rotation members having incremental MD and BL rotational offsets. The set of rotation members may include an array of MD and BL angles allowing adjustment of one of the MD and BL rotational alignments while holding the other of the MD and BL rotational alignments. The set of rotation members may include an array of 0°, 3°, and 7° MD angles, and 0°, 4°, and 10° BL angles.

The method may further include the step of preparing a temporary crown based on the surgical guide alignment. The base may be metal. The translation member may be injection molded plastic. The rotation member may be injection molded plastic.

Another aspect of the present invention is directed to a surgical guide assembly for positioning a drill bit during a dental implant procedure, the guide assembly including: a mounting member configured to mount to one or more teeth adjacent to an edentulous area; a base connected to the mounting member and dimensioned to extend over the edentulous area; a translation member adjustable with respect to the base; and a rotation member adjustable with respect to the translation member, said rotation member including an aperture configured to receive a radiographic marker or a drill. The translation and rotation members may be configured to adjust one of the mesio-distal (MD) rotational alignment and the buccal-lingual (BL) rotational alignment of the radiographic marker inserted in the aperture while holding the other of the MD and BL rotational alignment mechanically fixed. Also, the translation and rotation members may be configured to adjust the other of the MD and BL translational alignment of the radiographic marker while holding said one of the MD and BL translational alignment mechanically fixed.

The base, translation member and rotation member may be configured to adjust one of the MD translational alignment and the BL translational alignment of the radiographic marker while holding the other of the MD and BL rotational alignment mechanically fixed, and may be configured to adjusting the other of the MD and BL translational alignment of the radiographic marker while holding said one of the MD and BL translational alignment mechanically fixed.

The mounting member may be formed of an impression material spatially setting the base relative to the edentulous area. The base and the translation member may be configured such that the translation member can adjustably translate in a longitudinal direction relative to the base member for adjustment of MD translational alignment.

The translation member may be selected from a set of translation members having incremental MD offsets, wherein MD translational alignment may be adjusted by selecting a respective one of said set having a desired MD offset. The set of translation members may be reversible such that turning a respective one of said set upside-down provides a negative MD offset. The translation member and the rotation member may be configured such that the rotation member can adjustably translate in a lateral direction relative to the translation member for adjustment of BL translational alignment.

The rotation member may be selected from a set of rotation members having incremental MD and BL rotational offsets. The set of rotation members may include an array of MD and BL angles allowing adjustment of one of the MD and BL rotational alignments while holding the other of the MD and BL rotational alignments. The set of rotation members may include an array of 0°, 3°, and 7° MD angles, and 0°, 4°, and 10° BL angles. The set of rotational members may be reversible such that turning a respective one of said set upside-down provides a negative MD and/or BL angle.

The base may be metal. The translation member may be injection molded plastic. The rotation member may be injection molded plastic.

The alignment method and guide of the present invention have other features and advantages which will be apparent from or are set forth in more detail in the accompanying drawings, which are incorporated in and form a part of this specification, and the following Detailed Description of the Invention, which together serve to explain the principles of the present invention.

BRIEF DESCRIPTION OF THE DRAWINGS

FIG. 4 is an exploded view of the alignment assembly of FIG. 3.

FIG. 5 is an enlarged perspective view of a translation member of the alignment assembly of FIGS. 1A and 1B within a set of translation members used in combination with the alignment assembly of FIGS. 1A and 1B.

FIG. 6A is a perspective view of a rotation member of the alignment assembly of FIGS. 1A and 1B, and FIG. 6B is a plan view of a set of rotation members used in combination with the alignment assembly of FIGS. 1A and 1B.

DETAILED DESCRIPTION OF THE INVENTION

Reference will now be made in detail to various embodiments of the present invention, examples of which are illustrated in the accompanying drawings and described below. While the invention will be described in conjunction with exemplary embodiments, it will be understood that present description is not intended to limit the invention to those exemplary embodiments. On the contrary, the invention is/are intended to cover not only the exemplary embodiments, but also various alternatives, modifications, equivalents and other embodiments, which may be included within the spirit and scope of the invention as defined by the appended claims.

For the purposes of the present discussion, an implant site is defined as a region around an edentulous area where a dental prosthetic is to be placed, or a region around an area that is designed to become an edentulous area when the study is done while the tooth to be replaced is still present. The implant site also includes the adjacent gum tissue and underlying jawbone. The edentulous area is defined by a gap formed by an absence of a tooth. The edentulous area lies above the site where the implant abutment is. The prosthetic tooth eventually resides in and takes up the edentulous area.

In accordance with the present invention, an alignment template is configured to be placed within a patient's mouth and provide guidance for controllably and quantifiably adjusting the necessary drill trajectory. For example, the present invention allows for controllable and quantifiable mesio-distal alignment and buccal-lingual alignment of a drill guide which establishes the desired drill trajectory. For the purpose of clarity, the mesio-distal (MD) direction is the direction from the front of the mouth to the back, and the buccal-lingual (BL) direction is the direction extending from the cheek to the tongue.

Figure 1A:
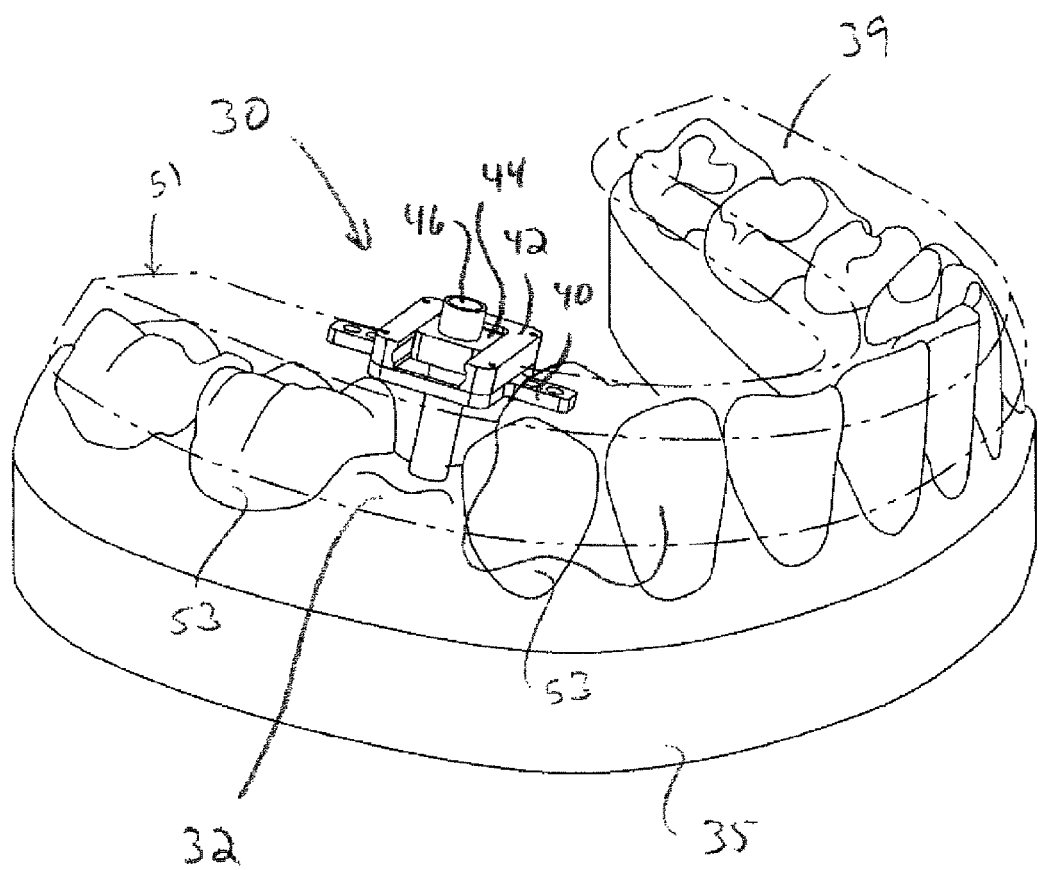
FIGS. 1A and 1B are perspective views of an alignment assembly mounted on a model of a dental implant site in accordance with the present invention, FIG. 1A illustrating one mounting member, and FIG. 1B illustrating another mounting member.
Figure 1B:
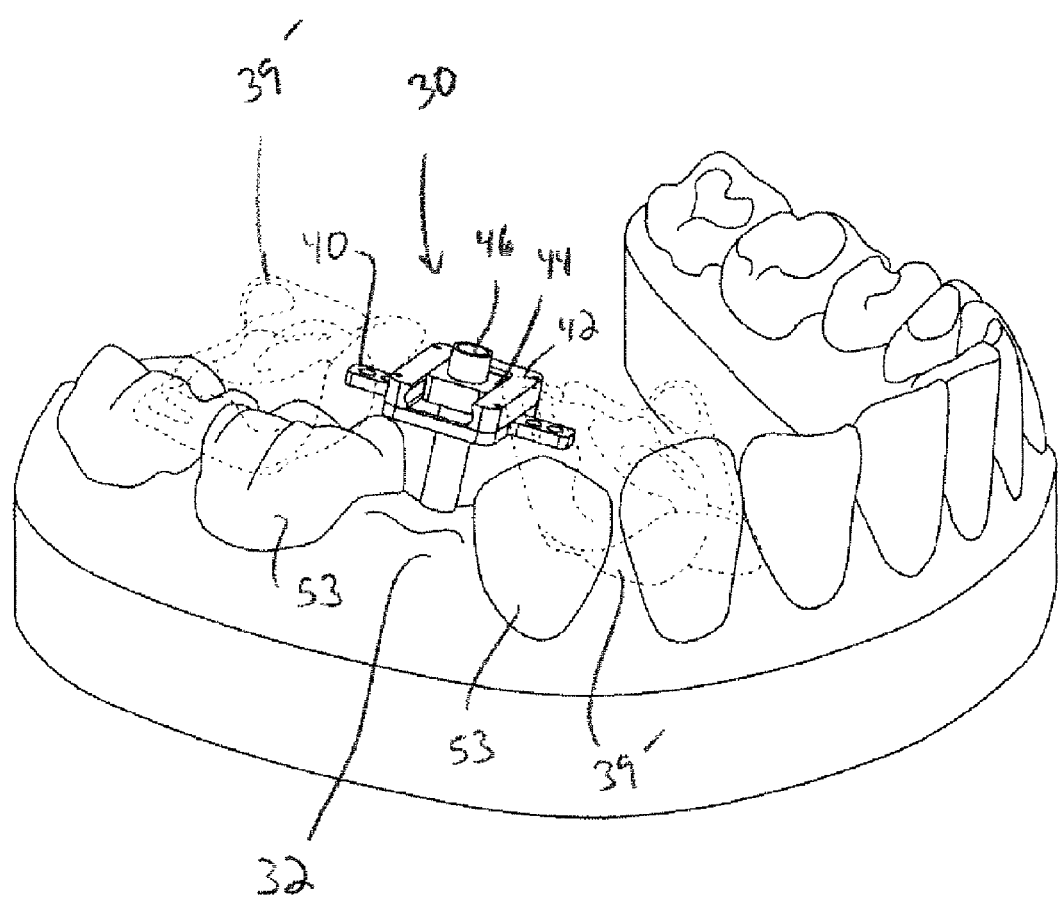
Figure 2:
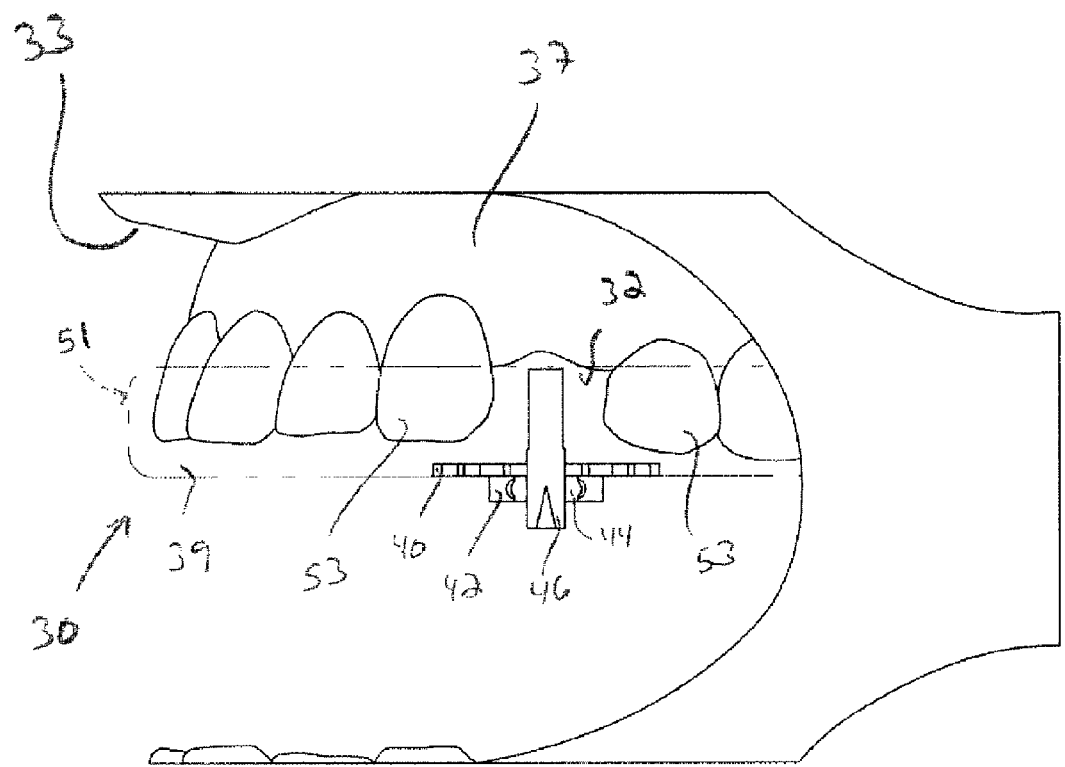
FIG. 2 is a side view of the alignment assembly of FIGS. 1A and 1B fitted on a patient's teeth.
Figure 3:
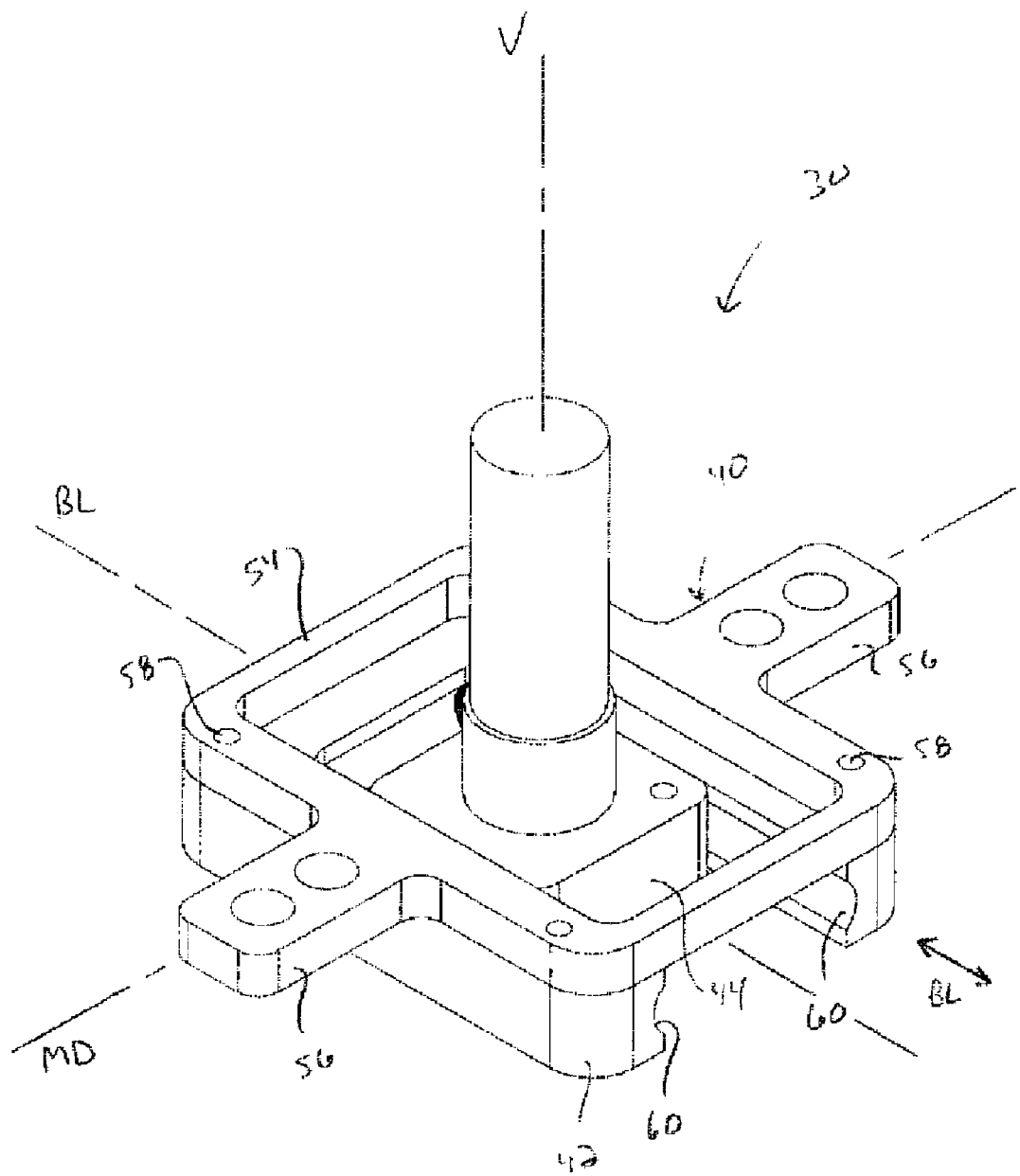
FIG. 3 is an enlarged perspective view of a portion of the alignment assembly of FIGS. 1A and 1B.

Turning now to the drawings, wherein like components are designated by like reference numerals throughout the various figures, attention is directed to FIGS. 1 and 2 which show an exemplary alignment assembly, generally designated by the numeral 30, in accordance with the present invention. In FIG. 2, the alignment assembly is shown in place over an edentulous area 32 within a patient's mouth 33, while in FIG. 1, the alignment assembly is shown in place over the corresponding edentulous area on a cast model 35 of the patient's upper jaw 37. The alignment assembly generally includes a mounting member 39, a base member 40, a translation member 42, a rotation member 44, a radiographic implant replica (RIR) 46, and optionally, a drill guide 47 (see FIG. 8). An enlarged view of the alignment assembly, sans mounting member, is shown in FIG. 3, and an exploded view thereof is shown in FIG. 4.

The mounting member may be in the form of a mostly conventional custom-molded template fitting at least a portion of the patient's dental arch 49. Preferably, the mounting member may be a monolithically formed member closely conforming to the shape of at least a portion of the dental arch in a relatively conventional manner. For example, mounting member 40 may be a custom-molded plastic template 51 corresponding to the patient's entire dental arch, as shown in phantom in FIGS. 1 and 2. Alternatively, the template may be configured to extend along and over one or more teeth on either side of the edentulous area. In either case, the plastic template is configured to releasable secure one or more teeth 53 adjacent the edentulous area 32. Preferably, the mounting member is configured to engage at least one tooth on either side of the edentulous area, and more preferably engage a sufficient number of teeth to provide a stable platform when the mounting member is mounted on the patient's teeth or on the cast model thereof. One will appreciate that an aperture may be drilled or otherwise formed through the mounting member to provide access to the edentulous area, as will become apparent below.

Base member 40 is a relatively rigid member that is secured to the mounting member and is dimensioned to bridge the edentulous area. Suitable materials for the base member include metals, alloys, acrylics, thermoplastics and other relatively rigid materials. Preferably the base member is set in mounting member 39. For example, custom-molded plastic template 51 may be formed in situ about the base member. Alternatively, the base member may be adhered or otherwise fastened to the mounting member by otherwise conventional means. Regardless the method of securing the base member to the mounting member, the base member is securely affixed to the mounting member such that the base member also provides a stable platform relative to the patient's teeth as well as the model thereof. Alternatively, the mounting member may be a fabricated from a vacuum formed sheet, formed of a rigid bite registration material, or formed by other suitable means.

In one embodiment, the mounting member is formed of a rigid bite registration or impression material. In this embodiment, base member 40 is manually positioned, by eye, over the edentulous area 32 in a desired initial position. A suitable material such as BLU-MOUSSE® (Parkell, Inc.) is injected over the adjacent teeth and around the base member. During application, the mousse-like consistency of BLU-MOUSSE® allows the material to surround and conform with the adjacent teeth as well as the shape of the base member. Once applied, the material hardens to a plaster-like hardness providing a relatively rigid member solidly positioning the base member with respect to adjacent teeth 53 and, in turn, with respect to edentulous area 32.

With reference to FIGS. 3 and 4, The base member has a central rim 54 dimensioned and configured to bridge edentulous area 32 and further includes diametrically opposed legs 56 extending from the central rim. Preferably, the base member has a length that is at least approximately that of three typical teeth such that base member extends across the edentulous area and at least a portion of the adjacent teeth. One will appreciate that longer legs or additional structure may be provided for those instances where the edentulous area is formed by two or more missing teeth and multiple implants are to be placed adjacent one another therein. One will also appreciate that the mounting member may also be configured as an adjustable assembly to more precisely correspond with the actual distance necessary to extend across the edentulous area and overlap the adjacent teeth. One will further appreciate that the base member may take various other shapes and configurations so long as it provides a framework or base structure with sufficient structural integrity to solidly secure the translation member and, in turn, the rotation member to the mounting member.

With reference to FIGS. 3 and 4, translation member 42 is in turn mounted to base member 40. In the exemplary embodiment, the translation member is secured to base member by protrusions which correspond with engagement holes 58 in the base member. One will appreciate that the translation member may affixed to the base member by other suitable means such as tongue-and-groove structures, dovetail structures, pins, adhesives and other suitable fastening means.

In an exemplary embodiment, translation member 42 is a U-shaped member that slideably receives rotation member 44 to allow BL movement of the rotation member. In the exemplary embodiment, the translation member includes grooves 60 within the U-shape which are dimensioned and configured to receive corresponding tongues 61 of the rotation member. The rotation member is adjustable in the BL direction with respect to the translation member such that the rotation member may be set at a specific position. For example, stiff polyvinyl siloxane (PVS) resin my be used to affix the rotation member relative to the translation member and thus set the rotation member's position. Positioning of the rotation member will be discussed in more detail below.

With reference to FIG. 5, a set of translation members may be provided to facilitate adjustment in the MD direction of the rotation member. For example, grooves 60 of translation member 42 are substantially symmetrical with respect to the overall shape of the translation member such that rotation member 44 is centered with respect to base member 40. Grooves 60' of translation member 42' are offset in the MD direction (MDO) with respect to the overall shape of the translation member. Grooves 60" are further offset, and grooves 60''' further still. In the exemplary embodiment, the translation members have MD offset positions of 0 mm, 0.5 mm, 1.0 mm, and 1.5 mm to incrementally adjust RIR 46 to the front of the edentulous area. Accordingly, one may incrementally offset rotation member 44 and, in turn, RIR 46 as desired. By reversing the translation member, one may incrementally adjust the available MD positions toward the rear of edentulous area effectively providing MD offset positions of −0.5 mm, −1.0 mm, and −1.5 mm, thus doubling the range of adjustability and providing an overall adjustment range of 3.0 mm. One will appreciate that the incremental offsets may vary to in order to increase or decrease the range of MD translational adjustability.

Other means may be used to adjust the position of the translation frame relative to the base member. For example, the translation member and/or the base member may have has indexing holes to allow the adjustability of the MD. Preferably, the indexing holes are equidistantly arranged and located at discrete, known positions.

Turning now to the rotation member, rotation member 44 includes a bore 63 extending from a top end to a bottom end of the rotation member as shown in FIG. 4. The bore is dimensioned and configured to receive the radiographic implant replica (i.e., RIR 46) during the prosthetic study and laboratory processing. The RIR may be frictionally engaged within the bore or otherwise incrementally secured using detents or other suitable engagement means. The RIR acts as a radiographic marker in a CT scan or X-ray. By extending the trajectory of the implant replica into the bone area one can study the MD relation of bore 63 to neighboring teeth 53. The RIR is preferably made of a radio opaque material such as metal. An optional aiming rod integrated with the RIR may be provided to aid in positing an X-ray tube perpendicular to the implant site.

Figure 8:
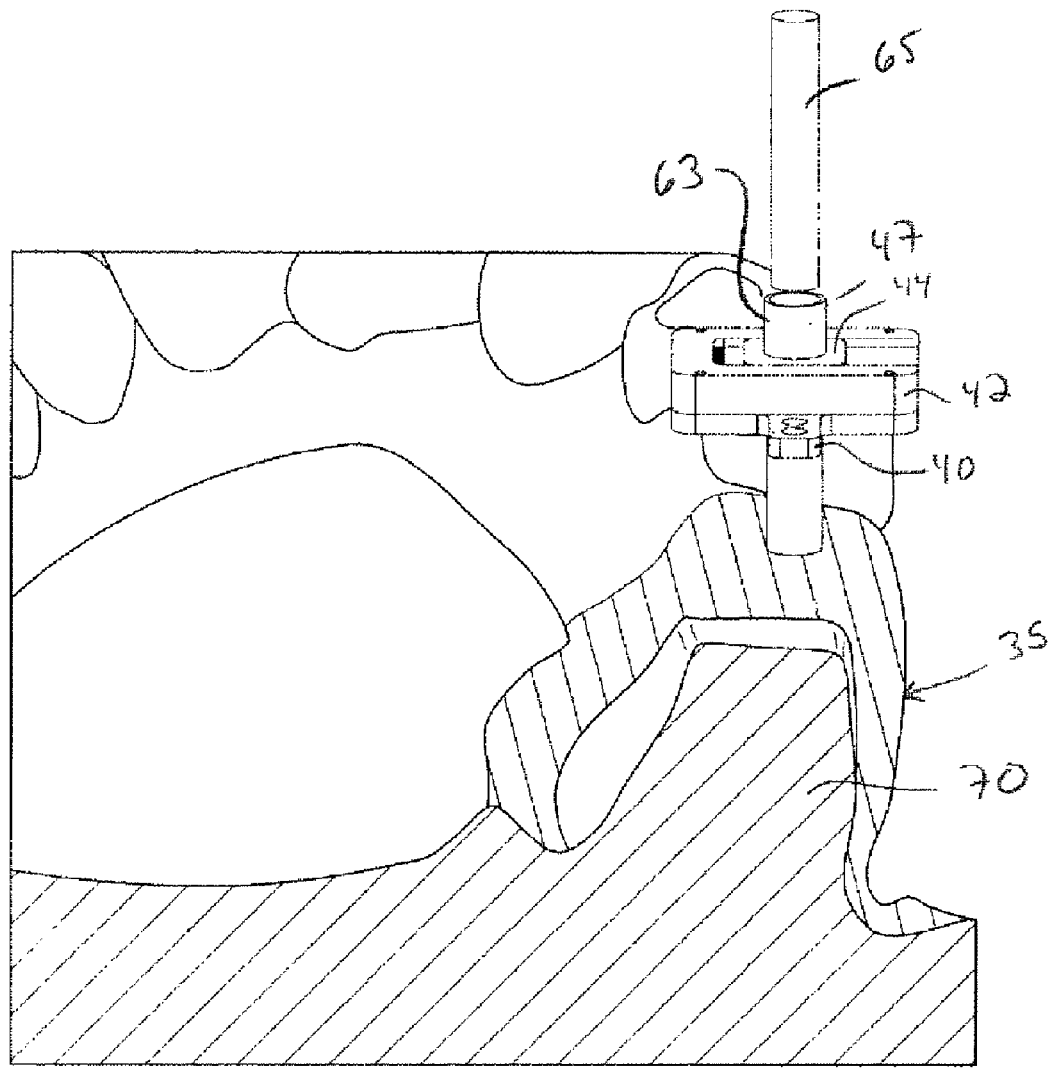
FIG. 8 is a cross-sectional view of the portion of the alignment assembly shown in FIG. 3 positioned relative to the model of FIGS. 1A and 1B.

Bore 63 is also configured to receive and guide a drill bit 65 during the osteotomy (see FIG. 8). In order to prevent the drill bit from destroying the walls of the bore, drill guide 47 may be inserted through the bore to precisely set the trajectory of the drill bit. Preferably, the drill guide is composed of a relatively hard and strong material such as metal and configured to guide the drill bit. One will appreciate that other suitable materials may be used including, but not limited to, injection molded plastics and the like.

With reference to FIG. 6, a set of rotation members 44 are provided to allow angular adjustment of the RIR and, in turn, the drill bit. The rotation members have bores with distinct angles from the longitudinal axis in both the MD and BL directions. In the exemplary embodiment, a set of rotation members are provided which allow trajectory adjustment at 0, 3, or 7 degrees in the MD plane and 0, 4, and 10 degrees in the BL plane. For the purposes of the present application, the MD plane refers to a vertical plane extending in the MD (front-to-back) direction, while the BL plane refers to a vertical plane extending in the BL (cheek-to-tongue) direction. Furthermore, and similar to the translation member discussed above, the rotation member may be reversed by removing it from translation member 42, flipping it over, and placing it back in the translation member to angle in the opposite direction. Thus, with the exemplary set of rotation members, the rotation angles available in the MD plane are −7, −3, 0, 3, and 7 degrees, while the rotation angles available in the BL plane are −10, −4, 0, 4, and 10 degrees. One will appreciate that the number and incremental offsets may vary to in order to increase or decrease the range of angular adjustability.

In the exemplary embodiment, the translation members and rotation members are made of injection molded plastic. One will appreciate that these members may be formed of other suitable materials such as metals and alloys. Also, the translation members and rotation members may be marked, such as by color-coding or other suitable indicia 67, to easily identify the incremental translations and incremental angles and avoid the risk of confusion. For example and with reference to FIG. 6B, a set of rotation blocks may be colored green, yellow and red to respectively identify their 0°, 3°, and 7° MD angles (as indicated by the letters "G", "Y", and "R", respectively), and provided with one, two, and three indicia dots to respectively identify their 0°, 4°, and 10° BL angles (as indicated by 67, 67', and 67", respectively).

The method of positioning the implant abutment and prosthetic can now be described. Preferably, the angle and translation of the desired trajectory is determined first within the MD plane, that is, a substantially vertical plane extending in the MD (i.e., front-to-back) direction (e.g., the plane formed by the intersection of MD axis and V axis in FIG. 3). The angle and translation within the MD plane may be clinically determined, that is, set by a surgeon, dentist or laboratory technician while the alignment assembly is fitted to a patient's dental arch. Such angle and translation may be verified by means of a radiograph. Next the angle and translation of the desired trajectory is determined within the BL plane, that is, a substantially vertical plane extending in the BL (i.e., cheek-to-tongue) direction. As opposed to the MD plane, however, BL angle and translation is preferably derived with the use of a cast model of the patient's dental arch. One will further appreciate that the BL settings may be determined before the MD settings. However, determining the MD settings during the patient's initial visit greatly benefits efficiencies both for the patient and the surgeon.

Preferably, the desired height of the implant are determined after the MD and BL settings are determined. In particular, the vertical position of the implant platform in relation to the osseous crest is generally determined after the MD and BL translations and rotations have been set.

The method of preparing the surgical guide for placing a dental implant may start with preparing model 35 of a site where a dental implant is to be placed. The model may be fabricated in a conventional manner. For example, an ACCU-TRAC® model base (Coltène/Whaledent Inc.), a pindexed cast, or other suitable three-dimensional model may be fabricated. Once the model is prepared, soft tissue depth measurements may be obtained and transferred to the model and the model is reduced and/or marked accordingly.

Concurrently, a custom-molded template 51 of the patient's dental arch may be prepared with base member 40 affixed thereto. As noted above, the custom-molded template may be formed in-situ about the base member, or the base member may be affixed thereto by in a suitable manner.

During the initial patient visit, the alignment assembly 30 may also be prepared as shown in FIG. 1 such that RIR 46 is positioned in a neutral position, that is, a position in which the trajectory of RIR is substantially normal to edentulous area, or in which the trajectory is an initial desired trajectory as determined by the oral surgeon, dentist or technician. For example, a zero-offset translation member 42 may be mounted on base member 40, a 0° MD/0° BL rotation member 44 inserted into the translation member, and RIR 46 inserted into the rotational member. The neutral position alignment assembly may then be mounted or fitted on the patient's dental arch model 35 over edentulous area 32 such that mounting member 39 engages with at least the teeth neighboring the edentulous area to securely hold the custom-molded template 51 in place and thereby providing a stable platform to adjust the trajectory.

Figure 7A:
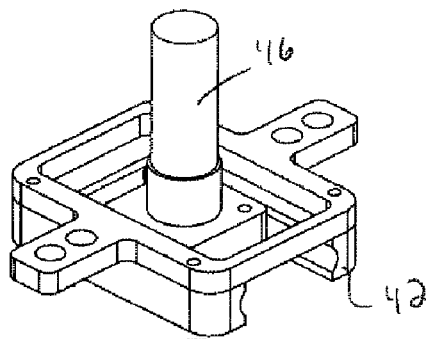
FIGS. 7A, 7B, 7C, 7D and 7E are perspective views of a portion of the alignment assembly of FIGS. 1A and 1B illustrating discrete adjustments thereof.
Figure 7B:
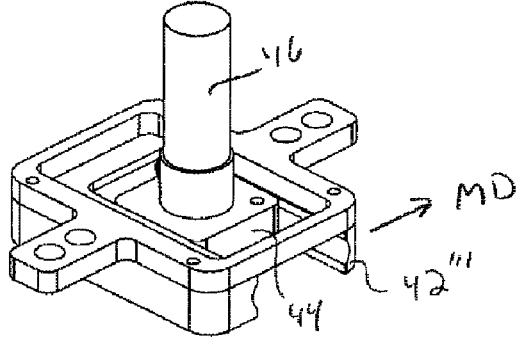
Figure 7C:
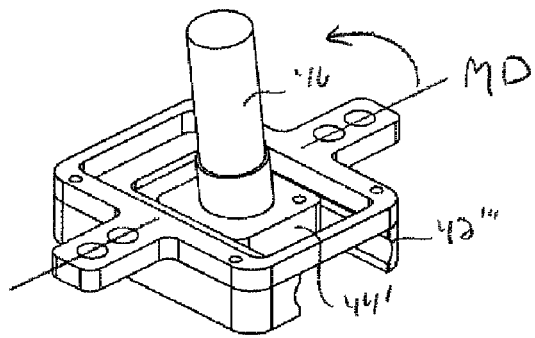

Once the alignment assembly has been prepared and the initial desired trajectory set, the surgeon, dentist or technician surveys the implant site and determines an initial desired trajectory (see FIG. 7A). By means of a radiograph, the RIR trajectory may be studied, and the translational and rotational adjustments may be noted. In the exemplary embodiment, the user first adjusts the MD translation of the RIR by removing zero-offset translation member 42 and substitute therefor an appropriate translation member, for example, a 0.5 mm offset translation member. In the event the offset is not enough, the user may then further adjust the translation of the RIR by removing the 0.5 mm offset translation member and replace it with a 1.0 mm offset translation member, and repeat again if 1.5 mm proves necessary (see, e.g., FIG. 7B, translation member 42'''). The user may then adjust the rotational alignment of RIR 46 in the MD plane by removing a 0° MD/0° BL rotation member 44 and substituting therefor an appropriate rotation member, for example the 3° MD/0° BL rotation member. Should the 3° adjustment prove insufficient, the user may remove the rotation member and replace it with a 7° MD/0° BL rotation member (see, e.g., rotation member 44' FIG. 7C). Alternatively, the translation may be adjusted one or more times before and/or between rotation adjustments, or vise versa. As such, the user may rotate or translate the RIR in a single direction at any one time, thus providing controlled and quantifiable adjustment of the RIR within the MD plane.

Once MD translation and rotation are set, the alignment assembly may be fitted to the patient's teeth and the user may take an X-ray or radiograph with the RIR in place in order to verify MD translation and rotation are appropriate. The user may then evaluate whether the MD direction should be further adjusted and, if necessary, repeat one or more steps of the above process.

After the MD direction is verified, alignment assembly 30 may be mounted on model 35 in order to set the BL translation and rotation. As noted above, soft tissue depth measurements may be transferred to the transversely cut model and the model is reduced and/or marked accordingly to illustrate the approximate depth and orientation of the underlying jawbone. One will appreciate that other suitable means may be utilized to determine the approximate location of the jawbone including, but limited to, the use of a CT scan.

Figure 7D:
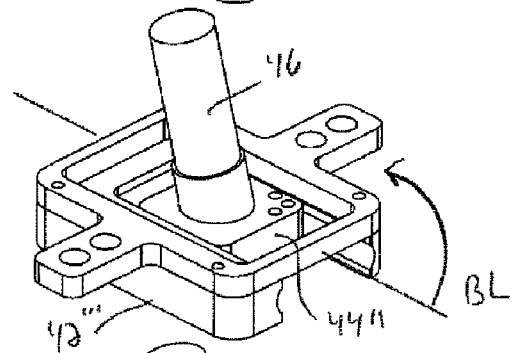
Figure 7E:
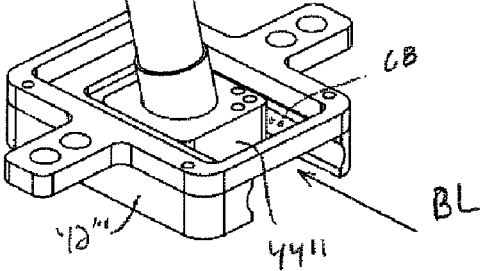

Knowing the general location and cross-section of the jawbone underlying the edentulous area, the user may then adjust the BL rotation as necessary to substantially align the RIR with modeled jaw bone. For example, the clinician may adjust the BL angle of the RIR by removing the 7° MD/0° BD rotation member and substituting therefor an appropriate rotation member, for example, a 7° MD/4° BD rotation member. It should be noted that the BL rotational adjustment selection is thus preferably made independently of the distinct MD adjustment as was clinically determined to be the correct MD correction. In this regard, "subsets" of rotation members are appropriately identified by color and/or by other suitable indicia. For example, one may quickly identify the exemplary 7° MD subset by its red color (indicated by the letter "R" in FIG. 6B). In the event the rotation is not enough, the user may then further adjust the BL rotation of the RIR by removing rotation member 44' and replacing it with 7° MD/10° BD rotation member (see, e.g., rotation member 44" FIG. 7D). The user may then adjust the BL translation by sliding the rotation member relative to the translation member (see FIG. 7E). Once the BL translation is sufficient, the user may secure the rotation member to the translation member by an adhesive, or by a suitable fastener. One will appreciate that the rotation member may be indexed within the translation member by detents 68 or other suitable means (see FIG. 7E).

In any event, the BL translation may be adjusted one or more times before and/or between BL rotation adjustments, or vise versa. As such, the user may rotate or translate the RIR in a single direction within the BL plane at any one time, thus providing controlled and quantifiable adjustment of the RIR within the BL plane.

For the purpose of clarity, the respective translations and rotations are illustrated in FIGS. 7A-7E with only the base, translation, and rotation members. One will appreciate that such adjustments may be made while the base member is securely affixed to either patient's dental arch or the cast model via the custom-molded template 51.

The RIR may be removed from rotation block 44 and replaced with drill guide 47. One will appreciate that the drill guide may be configured to set the drill depth in an otherwise conventional fashion. The alignment assembly is then placed back on the model as shown in FIG. 8. The drilling procedure is then modeled on the cast model by drilling through the bore as if the sleeve of the alignment assembly were in a patient's mouth. After a hole has been drilled in the model jaw bone 70, the user may evaluate the position of the alignment assembly.

If the hole is determined to be in a suitable position, the next step is to move to the patient's mouth. Now that the alignment assembly has been suitably aligned in the MD and BD directions, both rotationally and translationally, the alignment assembly, with the drill guide in place, may be used as a surgical guide.

The alignment assembly or surgical guide is then fitted within the patient's mouth. The template is then placed on the neighboring teeth in the same manner and position as on the model. The surgeon may make a final evaluation surveying the site and trajectory of the alignment assembly. Alternatively, the surgeon may replace the drill guide with the RIR and take an X-ray or radiograph again.

In comparison to conventional methods, the implant position determined by the alignment assembly may be readjusted with greater ease and flexibility. In order to readjust the alignment, the surgeon only needs to substitute the translation and/or rotation member and select a new alignment as described above. This alignment process can all be done while the patient waits in the chair.

Once the surgeon verifies that the alignment is correct and the drill guide 47 is in place, the surgeon may place a drill bit through the drill guide without damage the template. Based on the fixed MD and BL orientation, the alignment assembly will guide the drill bit into the jawbone in the exact position desired.

After the hole is drilled, an abutment and/or temporary crown may be implanted in an otherwise conventional fashion. If desired, the drill guide may further be used to guide in the abutment assembly.

In other embodiments, the alignment assembly may include various indexed positioning mechanisms fixed to the base. The positioning mechanisms may include tracks, linkages, or the like to incrementally translate or rotate the RIR in one degree of freedom while holding fast the remaining degrees of freedom. Such mechanisms allow the user to controllably and quantifiably incrementally adjust the RIR and thus ultimately align a drill guide along a desired trajectory.

Figure 9:
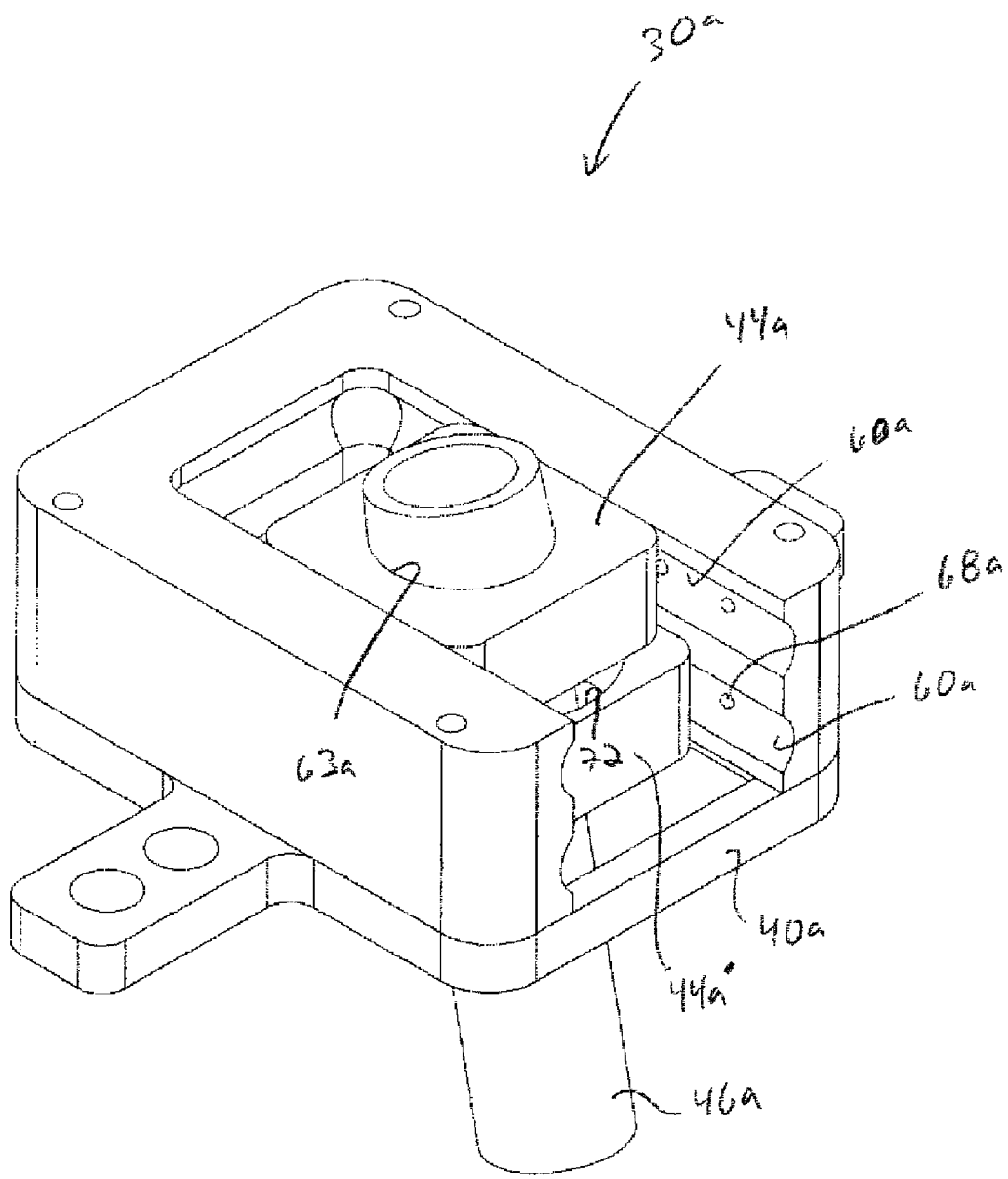
FIG. 9 is a perspective views of another alignment assembly in accordance with the present invention similar to that shown in FIG. 3.
Figure 10:
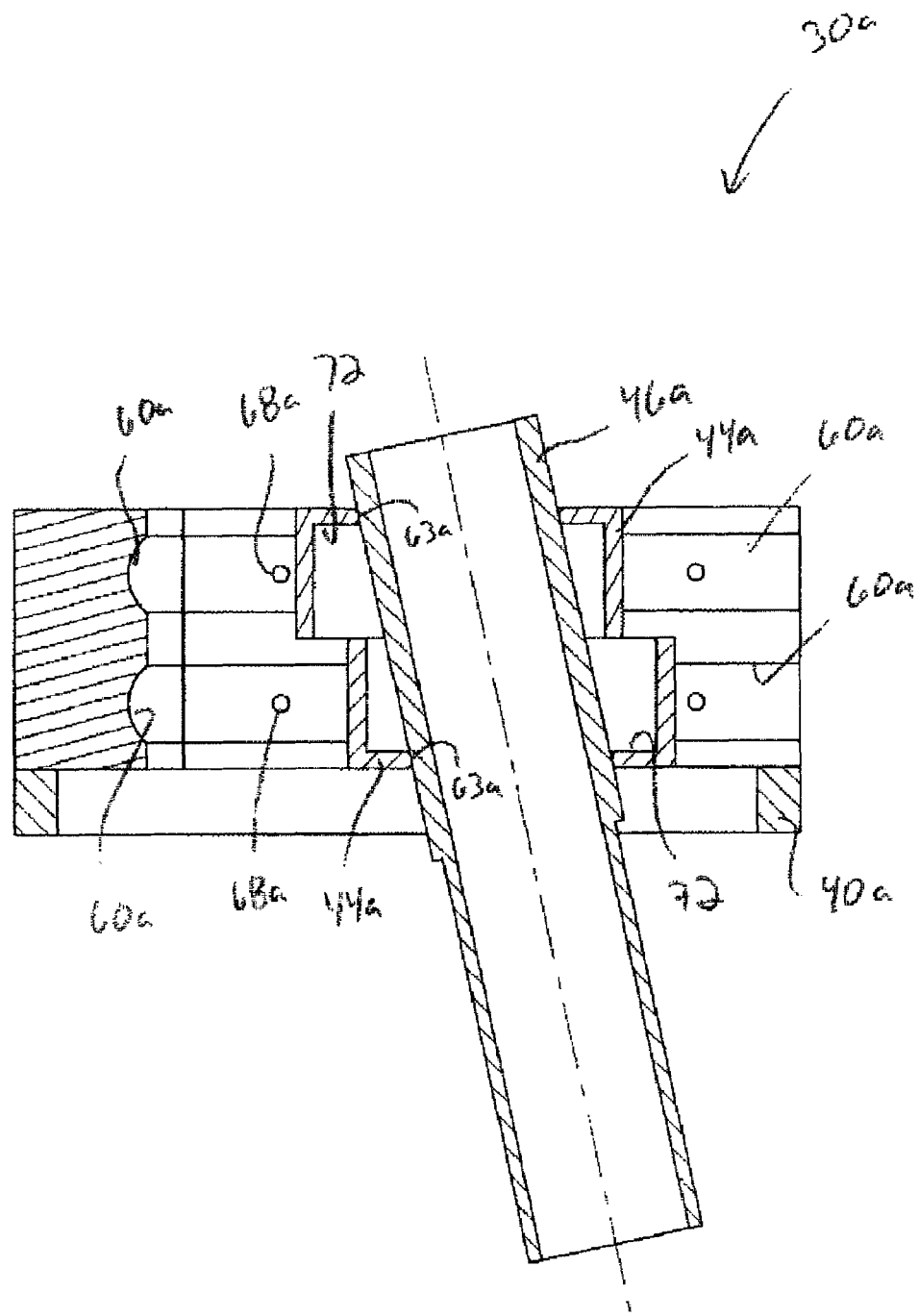
FIG. 10 is a cross-sectional view of the alignment assembly of FIG. 9.

For example, an alternative alignment assembly 30a is illustrated in FIGS. 9 and 10 that is similar to those described above but includes a modified rotation block assembly. Like reference numerals have been used to describe like components of alignment assembly 30 and alignment assembly 30a. In this embodiment, translation member 42a includes two sets of grooves 60a which receive two rotation members 44a, 44a' that are independently adjustable with respect to one another and the translation frame. In this exemplary embodiment, the rotation members have an inner cavity 72 which creates a relatively shallow bore 63a (see FIG. 10). Preferably the shallow bores are dimensioned to frictionally engage the RIR and/or other suitable means such as rubberized surfaces are provided to hold the RIR within the shallow bores. Such arrangement allows the rotation members to receive RIR 46a in an adjustable fashion. For example, the RIR may be rotated within the BL plane by moving upper rotation member 44a in one direction (e.g., to the left in FIG. 10) and/or moving lower rotation member 44a' in the other direction (e.g., to the right in FIG. 10). Similarly, the RIR may be translated in the BL plane by moving both the upper and lower rotation members in the same direction.

In operation and use, alignment assembly 30a is used in substantially the same manner as alignment assembly 30 discussed above. As rotation members 44a and 44a' allow for almost infinite adjustment of the BL rotation only one subset of rotation members are necessary. In this embodiment, one or more subsets of MD angle adjustment may be provided for adjustment of the MD angle (e.g., green "G", yellow "Y" and red "R" subsets, see FIG. 6b). As such, the MD rotation adjustment and the MD translation adjustment may be accomplished in the same manner discussed above. However, instead of replacing one rotation member for another, BL rotational adjustment and BL translational adjustment may be performed by moving rotation members 44a and 44a' relative to translation member 42.

The method and surgical guide of the present inventions has many advantages over conventional techniques. The surgical guide of the present invention provides a alignment assembly of relatively simple design which allows incremental, accurate, quantifiable and repeatable adjustments of drill trajectory. In part because each alignment direction is set in incremental individual steps, the above alignment method provides greater control and repeatability over conventional methods. The positional data is initially set on the cast model and directly transferred in each step. At each step in the process, the alignment is further refined. Most advantageously, MD alignment, MD rotation, BL alignment, and BL rotations adjustments are independently executed, thus preventing accidental change of one while adjusting another.

The use of a rotation member with indexed or fixed positions provides quantifiable positional information. Thus, the user will always know the last position and have the ability to return to that position if desired. This also allows the user to move in discrete increments. Instead of aligning the guide in free space each and every time, the above apparatus and method allows the user to move in small steps with finer adjustment. Instead of forcing the user to start with a clean-slate each time the alignment is modified, the alignment assembly in accordance with the present invention allows the user to adjust alignment in only the desired direction while holding alignment fixed in all other directions.

The method in accordance with the present invention provides for deliberate adjustments rather than haphazard movement resulting of poor control. If the user wants to adjust the rotation to 3 degrees from −3 degrees, the user need only remove the rotation member and flip it over. In contrast, with conventional methods, the user would have to carefully rotate the guide visually to an estimated −3 degrees and hope that the guide is positioned correctly at −3 degrees and has not further moved in any other direction in the process.

The use of parts with known alignment positions or index data provides the user with exact positioning and feedback on alignment. If a surgeon moves the rotation member in the MD direction laterally, he or she will know exactly how far it has been moved and the new location relative to the edentulous site.

Moreover, the above apparatus and method allows accurate translation or mapping of positioning information to the implant site. The final alignment of the surgical guide is the exact position desired. The implant, abutment, and provisional crown can be placed confidently during just the second patient visit. Complex instruments are further eliminated. Because of the accurate planning, all implants and components can be preordered, eliminating the need for inventory.

For convenience in explanation and accurate definition in the appended claims, the terms "up" or "upper", "down" or "lower", "inside" and "outside" are used to describe features of the present invention with reference to the positions of such features as displayed in the figures.

The foregoing descriptions of specific exemplary embodiments of the present invention have been presented for purposes of illustration and description. They are not intended to be exhaustive or to limit the invention to the precise forms disclosed, and obviously many modifications and variations are possible in light of the above teachings. The exemplary embodiments were chosen and described in order to explain certain principles of the invention and their practical application, to thereby enable others skilled in the art to make and utilize various exemplary embodiments of the present invention, as well as various alternatives and modifications thereof. It is intended that the scope of the invention be defined by the Claims appended hereto and their equivalents.

What is claimed is:

1. A method of preparing a surgical guide for positioning a dental implant relative to an implant site, said method comprising the steps of:

providing an alignment assembly, said alignment assembly including:
    a mounting member configured to mount to one or more teeth adjacent to an edentulous area of the implant site;
    a base connected to the mounting member and dimensioned to extend over the edentulous area;
    a set of translation members having incremental mesio-distal (MD) offsets, each translation member being adjustable with respect to the base; and
    a rotation member adjustable with respect to a respective one of the translation members, said rotation member including an aperture configured to receive a radiographic marker;

inserting the radiographic marker through the rotation member;

placing the alignment assembly at the edentulous area where the dental implant is to be placed;

adjusting the MD rotational alignment of the radiographic marker while the buccal-lingual (BL) rotational alignment is fixed;

adjusting the MD translational alignment of the radiographic marker while the BL rotational alignment is fixed;

adjusting the BL rotational alignment of the radiographic marker while the MD rotational alignment is fixed; and adjusting BL translational alignment of the radiographic marker while the MD translational alignment is fixed;

wherein the MD translational alignment is adjusted by replacing a first translation member of said set having a first MD offset with a second translation member of said set having a second MD offset to achieve a desired MD offset;

wherein the set of translation members and the rotation member are configured such that the rotation member can adjustably translate in a lateral direction relative to a respective one of the translation members for adjustment of the BL translational alignment; and wherein the rotation member is rotationally fixed when laterally adjusted within a respective one of the translation members.

2. A method of preparing a surgical guide according to claim 1 further comprising the steps of:

inserting a guide member in place of the radiographic marker;

modeling drilling of a jaw bone on a model of the implant site using the alignment assembly; and evaluating the position of the guide member relative to the implant site.

3. A method of preparing a surgical guide according to claim 1, further comprising the steps of:

fabricating a surgical guide based on the alignment assembly whereby a guide member in the alignment assembly is used to guide a drill in a mouth; and placing the surgical guide at the implant site.

4. A method of preparing a surgical guide according to claim 1, wherein the mounting member is formed of an impression material spatially setting the base relative to the edentulous area.

5. A method of preparing a surgical guide according to claim 1, wherein the base and the translation members are configured such that each of the translation members can adjustably translate in a longitudinal direction relative to the base member for adjustment of MD translational alignment.

6. A method of preparing a surgical guide according to claim 1, wherein the set of translation members are reversible such that turning a respective one of said set upside-down provides a negative MD offset.

7. A method of preparing a surgical guide according to claim 1, wherein the rotation member is selected from a set of rotation members having incremental MD and BL rotational offsets, wherein the MD and BL rotational offset is adjusted by replacing a first rotation member of said set having a first rotational offset with a second rotation member of said set having a second rotational offset to achieve a desired rotational offset.

8. A method of preparing a surgical guide according to claim 7, wherein the set of rotation members includes an array of MD and BL angles allowing adjustment of one of the MD and BL rotational alignments while holding the other of the MD and BL rotational alignments.

9. A method of preparing a surgical guide according to claim 8, wherein the set of rotation members includes an array of 0°, 3°, and 7° MD angles, and 0°, 4°, and 10° BL angles.

10. A method of preparing a surgical guide according to claim 1, further comprising the step of:

preparing a temporary crown based on the surgical guide alignment.

* * * * *